United States Patent [19]

Saeki et al.

[11] 3,957,894

[45] May 18, 1976

[54] CATALYTIC DIMERIZATION OF CONJUGATED DIENES

[75] Inventors: Kenji Saeki, Ohtake; Tetsuo Hayashi, Iwakuni, both of Japan

[73] Assignee: Mitsui Petrochemical Industries, Ltd., Tokyo, Japan

[22] Filed: Feb. 5, 1974

[21] Appl. No.: 439,692

[30] Foreign Application Priority Data

Feb. 10, 1973 Japan................................. 48-16106

[52] U.S. Cl............................................. 260/666 B
[51] Int. Cl.²....................................... C07C 3/035
[58] Field of Search ................................. 260/666 B

[56] References Cited
UNITED STATES PATENTS 3,377,397   4/1968   Maxfield ......................... 260/666 B

OTHER PUBLICATIONS

Hackh's Chemical Dictionary, McGraw–Hill, N. Y. 4th Edition, 1969, p. 459.

*Primary Examiner*—Veronica O'Keefe
*Attorney, Agent, or Firm*—Sherman & Shalloway

[57] ABSTRACT

In a method of producing a dimer with a six-membered ring by contacting a catalyst containing iron compounds and organoaluminum compounds with conjugated dienes, the improvements comprising using a catalyst comprising ferrous or ferric compounds organoaluminum compounds and nitric oxide.

10 Claims, No Drawings

CATALYTIC DIMERIZATION OF CONJUGATED DIENES

The present invention relates to improvements in producing six-membered ring dimers from conjugated dienes in the presence of a novel catalyst which is easy to formulate, easily reproducible in catalytic function, inexpensive and easily available, and which gives increased yields and high selectivity at mild reaction temperatures for a curtailed reaction time.

Catalytic dimerization has hitherto been known in which six-membered ring dimers are produced by contacting a catalyst containing iron compounds and oganoaluminum compounds with conjugated dienes such as butadiene and isoprene.

For instance, Japanese Pat. No. 16882/63 (German Pat. No. 1140569) discloses catalytic dimerization or trimerization of conjugated dienes. In this disclosure, the use of a catalyst is disclosed, which is prepared by reacting a compound of Fe, Co, or Ni, for example, iron acetylacetonate, with an organic compound of metals of groups I to III in the periodic table, e.g., an organoaluminum compound with the use of a Lewis base, preferably triphenylphosphine, as an electron donor. According to this disclosure, eight-membered ring cyclooctadienes as a primary product together with a small amount of vinylcyclohexenes with a six-membered ring are obtainable from butadienes. According to the examples disclosed, the highest percentage selectivity in the formation of dimers of six-membered rings is 41.3% based on the reacted butadiene and unfavorable by-products of non-volatile components amount to 32.8%.

In contrast, Japanese Pat. No. 3827/64 U.S. Pat. No. 3450732, BP No. 935716, FP No. 1320729) discloses catalysts useful for catalytic dimerization or trimerization of conjugated dienes. In this second disclosure, as an electron donor are used compounds of multiple carbon to carbon bonds or containing an atomic group having unbonded electron pairs such as cyclic olefins, conjugated olefins, acetylenes, diketones and alkyl or aryl compounds of group Va in the periodic table. The aforesaid catalyst is made by reacting organometallic compounds of groups Ib to IIIb of the periodic table, eg, trialkylaluminum or alkylaluminumalkoxide with transition metal compounds containing metal of an iron group, eg, iron acetylacetonate, in the presence of the aforesaid electron donors. The publication discloses that with the use of the aforesaid catalyst, butadiene can be converted into vinylcyclohexene, cyclooctadiene, 3-methylheptatriene and cyclododecatriene, but there is no description of an embodied reaction. As in the first disclosure, this catalytic system cannot produce dimers of six-membered rings highly selectively.

Further the processes for the formulation of catalysts of the first and second disclosures are complicated and reproducibility of catalytic conditions of the formed catalyst is unsatisfactory. The reaction temperature and time of catalytic dimerization or trimerization require more improvements.

Japanese Pat. No. 12297/66 published July 9, 1966 discloses a process for the production of a low polymer of a conjugated diolefin in the presence of a catalyst prepared from anhydrous iron chloride or iron acetylacetonate and an electron donor of the formula R$_3$M (R is an organic group or halogen and M is phosphorus.) Examples are triphenylphosphine and organometallic compounds selected from alkylzinc, alkylaluminum halide, alkylaluminum alkoxide, trialkylaluminum, etc.

In this third disclosure cyclic compounds are not substantially formed, for instance, a linear low polymer such as octatriene and methyl heptatriene is obtained from butadiene.

Japanese Pat. No. 7295/70, U.S. Pat. No. 3377397, BP No. 1150298, FP No. 1502141 and GP No. 1593268) discloses catalytic dimerization of butadiene and/or isoprene and a catalyst therefor. In this fourth disclosure there is used a catalyst prepared by mixing dinitrosyliron halide of the formula

$$Fe(NO)_2X$$

where X is a halogen with a reducing agent selected from Grignard reagents and alkyllithium in the presence of a third component. As the third component are listed tetrahydrofuran, triphenylarsine, triphenylstibine, pyridine, diphenyl sulfide, dibutyl sulfide, and thiophene.

In this fourth disclosure, the dinitrosyliron halide to be used for the preparation of the catalyst is difficult to obtain and its synthesis is difficult and complicated. The procedure of preparing the catalyst with the use of it requires complicated and skillful art. There is also a problem in achieving reproducibility of the activity of the catalyst.

J. Chemical Society (C) discloses on pages 1856 to 1860 (1968) catalytic dimerization of dienes by nitrocarbonyl transition-metal compounds. According to this report, dicarbonyldinitrosyliron of the formula Fe(CO)$_2$(NO)$_2$ or dicarbonylnitrosyl $\pi$-allyl) iron of the formula $\pi$-allyl-Fe(CO)$_2$NO are in use as catalysts. It is disclosed that the copresence of triethyl aluminum does not produce any advantage in catalytic function. This catalyst is also complicated or difficult to prepare and also has poor reproducibility of its catalytic activities. With respect to conversion and selectivity or formation of a six-membered ring, this catalyst leaves much room for improvement, and its reaction time is too long.

The inventors have tried to overcome the aforesaid disadvantages and faults of the prior disclosures and have found that catalysts comprising ferrous or ferric compounds, organoaluminum compounds, and nitrogen (nitric or nitrous oxide, are very easy to formulate. They can be formed by adding a simple step of introducing a nitric oxide gas into the Ziegler-type catalyst system comprising iron and oganoaluminum compounds. With the use of the catalyst, six-membered ring formation and dimerization of conjugated dienes can rapidly proceed under mild conditions. Conversion is high and the six-membered ring dimerized product is formed with a conspicuously high selectivity.

The formation of the catalyst is very easy and the activity, selectivity and reproducibility of the obtained catalyst are extremely good. The inventors have found that a process for production of a dimer with a six-membered ring from butadiene, suitable for large-scale production can be provided, and from the observations in catalytic dimerization of for instance isoprene, it is also found that selectivity of forming a six-membered ring dimer is remarkably high and selectivity of forming a specified dimer among obtainable six-membered ring dimers is very high.

Accordingly, the present invention provides a process for producing a six-membered ring dimer with the use of inexpensive, easily available, stable catalyst, which is easy to formulate and whose catalytic function is highly reproducible, at a mild reaction temperature for a shortened reaction time, and in increased yields with a high selectivity.

The catalyst to be used for the dimerization of conjugated dienes in the present invention can be formed with the addition of nitric oxide gas to the mixed system of ferrous or ferric compounds, and organoaluminum compounds. Formation of the catalyst is possible in the presence or absence of a dimerization reaction solvent. The catalyst may be preformed or formed in the presence or absence of conjugated dienes within the dimerization reaction area. For example, if nitric monoxide is introduced at as low a temperature as −40°C into a reactor containing a light brown solution which is prepared by reacting iron compounds in toluene at as low a temperature as −40°C under an inert gas atmosphere, e.g. nitrogen, the solution becomes dark brown within several minutes. After the reaction has been fully conducted, there is no occurrence of a brown gas caused by formation of nitrogen dioxide even if the reaction system is exposed to the air. This indicates that free nitric oxide (NO) is no longer present in the system and that a chemical reaction between iron compounds, organoaluminum compounds and NO gas has occurred. The chemical structure of the resultant is still unknown.

The aforesaid catalyst-forming reaction in the same manner as a catalytic dimerization reaction which is later described, is carried out in the substantial absence of molecular oxygen and moisture, preferably in an atmosphere of an inert gas such as nitrogen or argon. The presence of a slight amount of moisture causes no recognizable problem.

In forming the catalyst, it is preferable to contact ferrous or ferric compounds with organoaluminum compounds at room temperature or below, eg, about 25° to about −100°C. It is advisable that addition of nitric oxide gas be conducted at about 0°C or below, preferably about −20°C or below, eg, about −20°C to about −100°C. The time required for catalytic formation is not limited and ranges from several minutes to 1 hour. The order of addition of iron compounds, organoaluminum compounds and nitric oxide in forming the catalyst is not limited if all the procedures are taken at low temperatures, say −10°C or below.

In commercial production of the catalyst it will be convenient to form the catalyst in the dimerization reaction area in the presence of raw material conjugated dienes. In this embodiment, it is acceptable that the completion of formation of the catalyst is indistinguishable from the time of starting the dimerization reaction. For instance, ferrous or ferric compounds or their solution in the dimerization reaction solvent are added to a reactant containing at least one type of conjugated diene or its dimerization reaction solution and an organoaluminum compound is added to the resultant solution. Then an NO gas is added. In these steps, it is desirable that the organoaluminum compounds should be added at room temperature or below and the nitric oxide gas at about −20°C or below. The solution thus obtained is maintained at a temperature of about −10° to 150°C, preferably about 10 to 100°C, for several minutes and the reaction proceeds to form six-membered ring dimerization reaction products. The time of the dimerization reaction is not particularly critical, but ordinarily several minutes to about 5 hours will be enough for the complete reaction.

A dimerization reaction can be carried out in the presence of the reaction solvent or in the absence thereof. When the reaction solvent is present, a catalytic component, particularly organoaluminum compounds or an optional nonpolar organic solvent, which is unlikely to decompose the formed catalyst, can be used.

Useful dimerization solvents include aromatic hydrocarbons such as toluene, xylene and chlorobenzene, aliphatic hydrocarbons such as pentane, hexane, heptane and octane, alicyclic hydrocarbons such as cyclopentane, cyclohexane and methylcyclopentane and combinations thereof.

The dimerization reaction can be carried out under normal pressure or a naturally generated pressure condition and there is no need to apply pressure positively or negatively. It is possible, however, to apply pressure of about 10 kg/cm² or below if desired.

The reaction can be conducted by batchwise, continuous, or multistaged continuous operations. After the reaction a small amount of methanol is added to deactivate the catalyst, as is conventional in olefin polymerization operations using a Ziegler-type catalyst. The catalytic residue can be extracted with water. The object product can be separated or taken up by reduced pressure distillation or other distillation steps.

Ferrous or ferric compounds that can be utilized for the formation of the catalyst in the present invention are widely inorganic and organic compounds. Among these are: halides such as iron chloride, iron bromide and iron iodide; other inorganic salts such as iron sulfate and iron carbonate; iron hydroxide; carboxylic acid salts such as iron acetate and iron oxalate; chelate compounds such as iron acetylacetonate and ferrocene (bis-cyclopentadienyl iron). Useful organoaluminum compounds include trialkyl- or triphenylaluminums, and dialkylaluminum halides. This is in view of their conversion, high selectivity of forming a six-membered ring dimer and the substantial absence of by-products such as low polymers higher than a trimer or high polymers. Dialkylaluminum hydride (forming trialkylaluminum in the presence of olefin) can also be used. The aforesaid desired organoaluminum compounds are members selected from the group consisting of (A) compounds of the formula $$R_3Al$$

wherein each R stands for one of the group consisting of hydrogen, alkyl with 1 to 8 carbon atoms and phenyl and may be the same as, or different from, each other R, and (B) compounds of the formula $$R'_2AlX$$

where R' is alkyl with 1 to 8 carbon atoms and X is a halogen atom.

These organoaluminum compounds include trimethylaluminum, triethylaluminum, tripropylaluminum, triisopropylaluminum, tributylaluminum, triisobutylaluminum, trisec-butylaluminum, trihexylaluminum, triphenylaluminum, diethylaluminum chloride, dipropylaluminum chloride, diisopropylaluminum chloride, dibutylaluminum chloride, diisobutylaluminum chloride, di-sec-butylaluminum chloride, dihexylaluminum chloride, and dialkylaluminum halides other than dialkylaluminum chlorides. Any optional combinations thereof can also be used.

The amount of ferrous compounds in the present invention is preferably about 0.00001 to about 0.05 mole per mole of the conjugated diene and more preferably about 0.00001 to about 0.01 mole. The amount of the aforesaid organoalumimum compounds is preferably about 0.1 to about 1000 moles per mole of ferrous or ferric compounds and more preferably about 1 to about 50 moles. The amount of NO is preferably about 0.1 to about 5 moles per mole of the aforesaid organoaluminum compounds and more preferably about 0.5 to about 1.5 moles.

The conjugated dienes useful in the present invention include, but are not limited to, 1,3-pentadiene butadiene, isoprene, cyclopentadiene, cyclohexadiene and mixtures thereof when conjugated dienes which are structurally asymmetric such as isoprene are selected, an expected result will be produced, in that dimerzed products with a six-membered ring, (which is not the case with conventional Ziegler catalyst) are almost quantitatively obtained as a primary product.

EXAMPLE 1

In a nitrogen-substituted reactor 0.35 g of iron acetylacetonate was dissolved in 86 g of isoprene and cooled to −78°C. To this solution was added 1.37 ml of triethylaluminum and subsequently 192 ml of NO gas was introduced into the reactor. When the temperature of the solution was gradually raised to about 30°C, heat generation started and stopped after 1 hour. A small amount of methanol was then added to the solution, the catalyst was deactivated, and the catalyst residue was extracted with water. The organic layer was separated from the water layer and dried with sodium sulfate. Then reduced pressure distillation at 8 mmHg was conducted. Little residue could be found. The distillate was analyzed by gas chromatography, NMR, infrared spectrum, mass spectrum etc. The composition was 92.3% of 1,4-(or 2,4-) dimethyl-4-ethenyl-1-cyclohexene(dimer), 3.9% of 2-methyl-4-isopropenyl-1-cyclohexene(dimer), 2.8% of 1-methyl-4-isopropenyl-1-cyclohexene(dimer) and 1.0% residue. The conversion of the isoprene was 92%.

CONTROL 1

Similar to example 1, 0.35 g of iron acetylacetonate was dissolved in 86 g of isoprene and cooled to −78°C. To this solution was added 1.37 ml of triethylaluminum. Without the addition of NO, the temperature in the system was gradually raised and the solution was heated at 100°C for 5 hours. The solution then treated as in example 1 and reduced pressure distillation was conducted. The composition of the product was 5% of a dimer, 28% of tri- and tetra-mers and 67% of a high polymer. The conversion of isoprene was only 12%.

EXAMPLE 2

In 680 g of isoprene was dissolved 0.16 g of ferric chloride in an argon atmosphere and cooled to −40°C. 1.37 ml of triethylaluminum was added and 192 ml of NO gas was introduced. The temperature of the solution was gradually raised and reaction started around 20°C. Agitation was continued while cooling was being carried out with a water bath to avoid a vigorous reflux, and refluxing was stopped in about one hour after it was recognized that the reaction was almost completed. The generated solution was treated as in example 1 to obtain the object product. The product comprised 92.3% of 1,4-(or 2,4-) dimethyl-4-ethenyl-1-cyclohexene (dimer), 7.7% 1- and 2-methyl-4-isopropenyl-1-cyclohexene (dimer) and other compounds in trace amounts. The conversion of isoprene was 88%.

EXAMPLE 3

As in example 1, 19.6 g of butadiene was dissolved in 17.5 ml of toluene and 2.5 ml of toluene solution containing 0.18 g of iron acetylacetonate was added. The solution was cooled to −78°C. To this solution was added 0.69 ml of triethylaluminum and then 96 ml of NO gas was introduced. The resultant solution was allowed to stand still at 30°C for 2 hours. The solution was then treated as in example 1. About 99.1% of the distillate was 4-vinyl-1-cyclohexene (dimer). The conversion of butadiene was 90.8%.

EXAMPLE 4

In a nitrogen-substituted reactor, 0.18 g of iron acetylacetonate was dissolved in 50 ml of 1,3-pentadiene and cooled to −40°C. To this was added 0.69 ml of triethylaluminum, and then 96 ml of nitric oxide (NO) was introduced. The reaction was carried out at 40°C for 5 hours. Afterwards, as in example 1, the solution was treated to obtain the object product. The conversion of 1,3-pentadiene was 7.8% and the product was only dimers. The selectivity to 3-methyl-4(or 5)-t-propenyl-1-cyclohexene was 88%.

EXAMPLE 5

As in example 1, reaction was carried out at 30°C for 1 hour with the use of 0.60 ml of diethylaluminum chloride in place of triethylaluminum. Only a dimer was obtained and 86% of the product was 1,4-(or 2,4-) dimethyl-4-ethenyl-1-cyclohexene. The conversion of isoprene was 43%.

EXAMPLES 6 TO 11

In a nitrogen-substituted reactor, 5 mmoles of iron acetylacetonate were added to 10 ml (100 mmoles) of isoprene solution in 50 ml of toluene and 5 mmoles of iron acetylacetonate and the solution was then cooled to −40°C. Then 5 mmoles of various organoaluminum compounds as given in Table 1 were added and 96 ml (4.0 mmoles) of NO gas was introduced. The reaction was carried out about at 35°C for 3 hours. The test results are as given in Table 1.

Table 1

| | | | Selectivity (%) | | | |
| Example No. | Organo-aluminum compounds | Conversion % | 1,4-(or 2,4-) dimethyl-4-ethenyl-1-cyclohexene | 1- and 2-methyl-4-isopropenyl-cyclohexene | Low polymer higher than trimer | Polymer |
| --- | --- | --- | --- | --- | --- | --- |
| 6 | $Al(CH_3)_3$ | 90.8 | 91.5 | 8.5 | — | — |
| 7 | $Al(i-Bu)_3$ | 21.6 | 90.3 | 9.7 | — | — |

Table 1-continued

| Example No. | Organo-aluminum compounds | Conversion % | Selectivity (%) | | | |
|---|---|---|---|---|---|---|
| | | | 1,4-(or 2,4-) dimethyl-4-ethenyl-1-cyclohexene | 1- and 2-methyl-4-isopropenyl-cyclohexene | Low polymer higher than trimer | Polymer |
| 8 | Al(n-Hexyl)$_3$ | 32.3 | 91.0 | 9.0 | trace | — |
| 9 | Al(C$_2$H$_5$)$_2$Cl | 51.3 | 95.4 | 4.6 | — | — |
| 10 | Al(i-Bu)$_2$Cl | 5.1 | 92.8 | 7.2 | — | — |
| 11 | Al(phenyl)$_3$ | 25.3 | 92.3 | 7.7 | — | — |

What we claim is:

1. In a method of producing a dimer with a six-membered ring by contacting a catalyst containing iron compounds and organoaluminum compounds with a conjugated diene which is butadiene, isoprene, 1,3-pentadiene, cyclopentadiene or cyclohexadiene, the improvement comprising using a catalyst consisting essentially of the reaction product of:
   A. an iron compound selected from at least one of the group consisting of: iron chloride, iron bromide, iron iodide, iron sulfate, iron carbonate, iron hydroxide, iron acetate, iron oxalate, iron acetylacetonate, and ferrocene, present in from about 0.00001 to about 0.05 moles per mole of the conjugated diene;
   B. an organoaluminum compound selected from at least one of the group consisting of compounds having the formula R$_2$AlR' wherein each R is one of the group consisting of hydrogen, alkyl having 1 to 8 carbon atoms and phenyl, and R' is the same as R or is a halogen, with the proviso that when R' is a halogen each R is an alkyl having 1 to 8 carbon atoms, present in from about 0.1 to about 1,000 moles per mole of iron compound; and
   C. nitric oxide, present in from about 0.1 to about 5 moles per mole of organoaluminum compound.

2. The method of claim 1 wherein the conjugated diene and the catalyst are reacted at a temperature of from −10° to 150°C.

3. The method of claim 1 wherein the iron compound is first contacted with the organoaluminum compound at a temperature of from about −100° to about +25°C. and the nitric oxide is then added at a temperature of from about −100° to about 0°C.

4. The method of claim 1 wherein the catalyst components are added to each other at a temperature not above −10°C.

5. The method of claim 1 wherein the catalyst is formed in situ with the conjugated diene, the organoaluminum compound being added at room temperature or below and the nitric oxide gas at about −20°C. or below.

6. The method of claim 1 wherein a dimerization solvent is used during the reaction, and wherein said solvent is toluene, xylene, chlorobenzene, pentane, hexane, heptane, octane, cyclopentane, cyclohexane, methylcyclopentane, or combinations thereof.

7. The method of claim 1 wherein the iron compound is iron acetylacetonate or ferric chloride.

8. The method of claim 1 wherein the organoaluminum compound is triethylaluminum, diethylaluminum, trimethylaluminum, triisobutylaluminum, diisobutylaluminum chloride, or triphenylaluminum.

9. The method of claim 8 wherein the organoaluminum compound is triethylaluminum.

10. The method of claim 1 wherein the iron compound is present in from about 0.0001 to about 0.01 moles per mole of the conjugated diene, the organoaluminum compound is present in from about 1.0 to about 50 moles per mole of iron compound, and the nitric oxide is present in from about 0.5 to 1.5 moles per mole of organoaluminum compound.

* * * * *